United States Patent [19]

Yamamoto et al.

[11] 4,279,838

[45] Jul. 21, 1981

[54] PROCESS FOR THE PREPARATION OF AMINOARYL THIOPHOSPHATES AND AMINOARYL PHOSPHATES

[75] Inventors: Ryuichi Yamamoto, Shirogane; Masaaki Torisu, Suwa, both of Japan

[73] Assignee: Mitsui Toatsu Chemicals Inc., Tokyo, Japan

[21] Appl. No.: 120,863

[22] Filed: Feb. 12, 1980

[30] Foreign Application Priority Data

Apr. 16, 1979 [JP] Japan .................................. 54-45315
May 17, 1979 [JP] Japan .................................. 54-59694
Aug. 31, 1979 [JP] Japan .................................. 54-110263

[51] Int. Cl.$^3$ .......................... C07F 9/09; C07F 9/165
[52] U.S. Cl. ..................................... 260/968; 260/974
[58] Field of Search ...................... 260/968, 944, 974

[56] References Cited

U.S. PATENT DOCUMENTS 1,837,176  12/1931  ter Horst ............................... 260/974
3,100,790   8/1963  Oertel et al. .......................... 260/944

OTHER PUBLICATIONS

Wagner et al, "Synthetic Organic Chemistry", (1953), J. Wiley, pp. 678-679.
Kosolapoff, "Organo Phosphorus Chemistry", (1950), J. Wiley, pp. 239-240 & 228.
Buehler et al, "Survey of Organic Synthesis", (1970), p. 440.

Primary Examiner—Anton H. Sutto
Attorney, Agent, or Firm—Fisher, Christen & Sabol

[57] ABSTRACT

Disclosed is a process for the preparation of an aminoaryl thiophosphate or phosphate which comprises hydrolyzing an N-acetylaminoaryl thiophosphate or phosphate by heating it in an aqueous solution of a mineral acid. The N-acetylaminoaryl thiophosphate or phosphate can be obtained by condensing an anhydrous alkali metal salt of an N-acetylaminophenol with phosphorus thiochloride or phosphorus oxychloride at a high temperature in the presence of an inert organic solvent or by condensing an N-acetylaminophenol with phosphorus thiochloride or phosphorus oxychloride in the presence of an alkali metal hydroxide or carbonate, water, and an organic solvent.

15 Claims, No Drawings

PROCESS FOR THE PREPARATION OF AMINOARYL THIOPHOSPHATES AND AMINOARYL PHOSPHATES

BACKGROUND OF THE INVENTION (a) Field of the Invention

This invention relates to a process for the preparation of an aminoaryl thiophosphate or aminoaryl phosphate by hydrolysis of the corresponding N-acetylaminoaryl thiophosphate or N-acetylaminoaryl phosphate.

(b) Description of the Prior Art

Aminoaryl thiophosphates and aminoaryl phosphates are compounds that are important as intermediates for the manufacture of isocyanates dyestuffs, and the like.

In the prior art, one common process for the preparation of an aminoaryl thiophosphate or phosphate comprises forming a nitroaryl thiophosphate or phosphate by nitration of a triaryl thiophosphate or phosphate or by reaction of nitrophenol sodium with phosphorus thiochloride or phosphorus oxychloride, and then reducing the nitro groups to amino groups. However, this process involves a safety problem because of the explosive properties of nitroaryl thiophosphates or phosphates, p-nitrophenol sodium, and the like, and has the disadvantage of requiring a complicated procedure and great expenses. These reasons make the above process unsatisfactory for industrial purposes.

Alternatively, it is conceivable that an aminoaryl thiophosphate or phosphate is obtained by hydrolysis of an N-acetylaminoaryl thiophosphate or phosphate. One prior art process for the hydrolysis of such acetylamino groups comprises heating a starting material in an aqueous alkaline solution. However, when this process is applied to N-acetylaminoaryl thiophosphates or phosphates having phosphoric ester linkages, not only the acetylamino groups but also the phosphoric ester linkages undergo hydrolysis. As a result, the desired product is obtained only in low yield.

SUMMARY OF THE INVENTION

It is an object of the present invention to provide a process for the preparation of an aminoaryl thiophosphate or phosphate in which the desired product can be obtained in high yield.

It is another object of the present invention to provide a process for the preparation of an aminoaryl thiophosphate or phosphate in which the desired product can be obtained by simple operation and at low cost.

It is still another object of the present invention to provide a process for the preparation of an aminoaryl thiophosphate or phosphate in which a high yield of the desired product can be obtained from the corresponding N-acetylaminophenol or an alkali metal salt thereof.

According to the present invention, there is provided a process for the preparation of an aminoaryl thiophosphate or aminoaryl phosphate which comprises hydrolyzing an N-acetylaminoaryl thiophosphate or N-acetylaminoaryl phosphate in an aqueous solution of a mineral acid.

The aforesaid hydrolysis may be carried out in the copresence of a small amount of an alcohol to increase the rate of hydrolysis further and achieve a higher yield.

The N-acetylaminoaryl thiophosphate or phosphate can readily be prepared by condensing an anhydrous alkali metal salt of an N-acetylaminophenol with phosphorus thiochloride or phosphorus oxychloride in an inert organic solvent, preferably at a temperature of from 80° to 140° C., or by condensing an N-acetylaminophenol with phosphorus thiochloride or phosphorus oxychloride in the presence of an alkali metal hydroxide, water, and an organic solvent, preferably at a temperature of 80° C. or below.

DETAILED DESCRIPTION OF THE INVENTION

It has been found to our surprise that, if an N-acetylaminoaryl thiophosphate or phosphate is hydrolyzed in an aqueous solution of a mineral acid, hydrolysis of the phosphoric ester linkages is suppressed and only the acetylamino groups are selectively hydrolyzed to give a good yield of the corresponding aminoaryl thiophosphate or phosphate having primary amino groups. In addition, it has also been found to our surprise that, it this hydrolysis is carried out in the presence of a small amount of an alcohol, the reaction time is shortened and only the acetylamino groups are hydrolyzed without any appreciable hydrolysis of the phosphoric ester linkages, whereby the desired product can be obtained in very high yield and with good selectivity. The reason why the presence of an alcohol accelerates the hydrolysis seems to be that the acetic acid resulting from the hydrolysis of the acetylamino groups probably reacts with the alcohol to form its acetic ester.

Specific examples of the N-acetylaminoaryl thiophosphate or phosphate used in the process of the invention include the thiophosphoric or phosphoric esters of 3-acetylaminophenol, 4-acetylaminophenol, and substituted acetylaminophenols having at least one alkyl or chlorine substituent on the benzene nucleus, such as 2-methyl-4-acetylaminophenol, 2-chloro-4-acetylaminophenol, etc.; the thiophosphoric or phosphoric esters of condensed-ring or polynuclear acetylaminophenols such as various isomers of N-acetylaminonaphthol, 2-(4-hydroxyphenyl)-2-(4-acetylaminophenyl) propane, 4-hydroxyphenyl-4'-acetylaminophenylsulfone, etc.; and the like. The process of the invention can also be applied to N-acetylaminoaryl thiophosphates or phosphates having more than one acetylamino groups.

Specific examples of the mineral acid used in the process of the invention include hydrochloric acid, sulfuric acid, phosphoric acid, and the like. Among these mineral acids, hydrochloric acid is particulary preferred. The concentration of the mineral acid is preferably from 5 to 30% by weight and more preferably from 15 to 25% by weight. In the case of hydrochloric acid, its concentration is preferably from 5 to 30% by weight and more preferably from 15 to 25% by weight. The rate of hydrolysis is unduly low at concentrations of lower than 5% by weight. On the other hand, no appreciable increase in reaction rate is noted at concentrations of higher than 20% by weight and, therefore, it goes without saying that no benefits can be derived from the use of concentrations of higher than 30% by weight. In the case of sulfuric acid or phosphoric acid, its concentration is preferably from 10 to 30% by weight and more preferably from 15 to 25% by weight.

The amount of mineral acid used is preferably at least one equivalent and more preferably from 3 to 10 equivalent per mole of the acetyl group contained in the N-acetylaminoaryl thiophosphate or phosphate. In the case of hydrochloric acid, its amount is preferably at least one equivalent and more preferably from 3 to 5 equivalents per mole of the acetyl group. If the amount of hydrochloric acid used is less than 3 equivalents, the reaction rate is unduly low, while if it is greater than 5 equivalents, no appreciable increase in reaction rate is noted. In the case of sulfuric acid or phosphoric acid, its amount is preferably at least one equivalent and more preferably from 5 to 10 equivalents.

The reaction temperature at which the hydrolysis of the invention is carried out is preferably from 50° to 100° C. and more preferably from 70° to 90° C. The reaction time may vary according to the concentration and amount of mineral acid used and the reaction temperature, but is generally from 2 to 8 hours. It is undesirable to carry out the hydrolysis of the invention under unduly severe reaction conditions (in particular, at excessively high temperatures) because the phosphoric ester linkages may also be split. This possibility can be eliminated by using the above-defined reaction conditions.

Specific examples of the alcohol which is preferably used in the hydrolysis of the invention include lower aliphatic monohydric alcohols such as methanol, ethanol, isopropanol, etc. Among these alcohols, methanol and ethanol are particularly preferred. The amount of alcohol used is generally from 0.5 to 2 equivalents per mole of the acetyl group contained in the N-acetylaminoaryl thiophosphate or phosphate. However, it is preferable to use the alcohol in an amount of at least one equivalent per mole of the acetyl group.

Where the hydrolysis of the invention is carried out in the copresence of an alcohol, the resulting acetic acid reacts with the alcohol to form its acetic ester. Thus, it is preferable to remove the acetic ester continuously from the reaction system.

The completion of the hydrolysis can readily be confirmed by taking a sample from the reaction mixture and subjecting it to thin layer chromatography.

After completion of the hydrolysis, boiling water is added to the reaction mixture whereby the precipitate (consisting of the hydrochlorides of the resulting aminoaryl thiophosphate or phosphate and various by-products) is dissolved. Then, the resulting solution is added dropwise, under cooling, to water containing a sufficient amount of an alkali (e.g., sodium hydroxide) to neutralize the hydrochloric acid contained in the reaction mixture. Especially in cases where the preparation of a triester is desired, the solution is added to water containing at least one equivalent of an alkali per equivalent of the hydrochloric acid contained in the reaction mixture. Thus, the desired trisaminoaryl thiophosphate or phosphate precipitates while small amounts of by-products, such as thiophosphoric or phosphoric mono- and diesters, thiophosphoric or phosphoric acid, etc. remain in solution in water. The precipitate so formed is separated by filtration and then dried to obtain the desired product having a high purity. If the presence of small amounts of by-products in the resulting trisaminoaryl thiophosphate or phosphate does not interfere with its use, the reaction mixture obtained after completion of the hydrolysis may be cooled to a temperature of from 0° to 10° C. without being neutralized with aqueous alkali. The precipitate so formed is separated by filtration and then dried to obtain the desired product in the form of its hydrochloride.

The trisaminoaryl thiophosphate or phosphate thus obtained is typically a white crystalline powder having a purity of not less than 98% and can be used as an intermediate for the manufacture of isocyanates, dyestuffs, and the like.

The N-acetylaminoaryl thiophosphates or phosphates which are useful as starting materials in the process of the invention can preferably be prepared by either of the following two procedures.

Procedure A

In this procedure, an N-acetylaminophenol is reacted with phosphorus oxychloride or phosphorus thiochloride in the presence of an alkali metal hydroxide or carbonate, water, and an organic solvent.

Specific examples of the N-acetylaminophenol used as a starting material include the N-acetyl derivatives of 3-aminophenol, 4-aminophenol, and substituted aminophenols having at least one alkyl or chlorine substituent on the benzene nucleus, such as 2-methyl-4-aminophenol, 2-chloro-4-aminophenol, etc.; the N-acetyl derivatives of polynuclear aminophenols such as 2-amino-1-naphthol, 5-amino-1-naphthol, 6-amino-1-naphthol, 7-amino-1-naphthol, 7-amino-2-naphthol, 4-hydroxyphenyl-4'-aminophenyldimethylemethane, 4-hydroxyphenyl-4'-aminophenylsulfone, etc.; and the like. This procedure can also be applied to N-acetylaminophenols having more than one acetylamino group.

The organic solvent may be any of the organic solvents which have inertness to phosphorus oxychloride or phosphorus thiochloride and can dissolve the N-acetylaminophenol used as a starting material. Specific examples of such organic solvents include ketones such as acetone, methyl ethyl ketone, methyl n-propyl ketone, methyl n-butyl ketone, methyl isobutyl ketone, diethyl ketone, etc., ethers such as isopropyl ether, n-butyl ether, 1,4-dioxane, diethylene glycol, dimethyl ether, etc.; chlorinated aliphatic hydrocarbons such as chloroform, methylene chloride, ethylene dichloride, etc.; aromatic compounds such as benzene, toluene, xylene, diethylbenzene, monochlorobenzene, dichlorobenzene, etc.; and the like.

The alkali metal hydroxide or carbonate (hereinfter referred to as the alkali) is typically selected from the hydroxides and carbonates of sodium and potassium and suitably used in the form of an aqueous solution or suspension (hereinafter referred to as an alkaline water) containing the alkali at a concentration of from 20 to 60% by weight.

Preferably, the alkali is used in an amount equal to or slightly in excess of the stoichiometric amount, i.e. 3 moles per mole of the phosphorus oxychloride or phosphorus thiochloride.

As described above, the concentration of the alkali in the alkaline water is suitably from 20 to 60% by weight. If the concentration is lower than 20% by weight, the remaining chlorine atoms of the phosphorus oxychloride or phosphorus thiochloride and the resulting intermediate products (mono- and diesters) are apt to undergo hydrolysis. If it is higher than 60% by weight, the reaction rate is undesirably reduced to such an extent that the hydrolysis of phophorus oxychloride or phosphorus thiochloride in the alkaline water tends to proceed more rapidly than the esterification reaction. The preferred range of the concentration is from 30 to 50% by weight.

The N-acetylaminophenol and the phosphorus oxychloride or phosphorus thiochloride are used in a molar ratio ranging from 2.5:1 to 20:1. Generally the phosphorus oxychloride or phosphorus thiochloride, which will undergo some degree of hydrolysis during the reaction, may as well be used slightly in excess of the stoichiometric amount to enhance the yield based on the thereto dropwise over a period of 15 minutes. The resulting mixture was further stirred at that temperature for 30 minutes. Then, 50.7 g (0.3 mole) of phosphorus thiochloride was added thereto dropwise over a period of 1 hour and the reaction was carried out at 30° C. for 5 hours. After the acetone was distilled off at 60° C., the resulting concentrate was poured into 3,000 g of ice water at 0°–10° C. The resulting mixture was stirred for 30 minutes and then allowed to stand overnight. The precipitate so formed was separated by filtration, ground finely in a mortar, transferred to a beaker, and then suspended in 2,000 g of ice water and 90 g of a 45% aqueous solution of sodium hydroxide. The resulting suspension was stirred at 10°–20° C. for 2 hours. The precipitate was separated by filtration, washed with water, and then vacuum-dried at 80° C. for 10 hours to obtain 146.4 g of a white crystalline product melting at 193°–196° C. This product was tris(4-acetylaminophenyl) thiophosphate and its yield was 95% based on the amount of phosphorus thiochloride used.

(b) Hydrolysis of Tris(4-acetylaminophenyl) Thiophosphate

Into a 2-liter flask fitted with a stirrer, a thermometer, and a distillation column were charged 256.8 g (0.5 mole) of tris(4-acetylaminophenyl) thiophosphate, 521.4 g (5 moles) of 35% hydrochloric acid, 260.7 g of water, and 48 g (1.5 moles) of methanol. The resulting reaction mixture was heated to 85° C. and the hydrolysis was carried out at that temperature, during which the methyl acetate formed as a by-product was removed from the reaction system. When the reaction mixture was heated to 85° C., the tris(4-acetylaminophenyl) thiophosphate dissolved after a while but subsequently formed a white slurry again. After the hydrolysis was continued for 3 hours, a sample was taken from the reacton mixture and neutralized with dilute sodim hydroxide. When the precipitate so formed was dissolved in methanol and then analyzed by thin layer chromatography, insufficiently hydrolyzed intermediate products (or the products of partial hydrolysis of tris(4-acetylaminophenyl) thiophosphate still having one or two acetyl groups) were found to have disappeared almost completely and a spot representing the presence of a very small amount of 4-aminophenol was observed. The hydrolysis was stopped at this time and 400 ml of boiling water was added to the reaction mixture to dissolve the precipitate. The resulting solution was added dropwise to ice water containing 240 g (6 moles) of sodium hydroxide. This addition was carried out at 10°–20° C. over a period of about one hour, and the resulting mixture was stirred at that temperature for an additional hour. The precipitate so formed was separated by filtration, washed with water, and then dried to obtain 191.2 g of a white crystalline powder melting at 154.5°–155.5° C. This product was tris(4-aminophenyl) thiophosphate having a purity of 98.7% as determined by the diazotization titration method, and its yield was 98.7% based on the amount of tris(4-acetylaminophenyl) thiophosphate used. The results of elemental analysis of the product were as follows:

|  | C(%) | H(%) | N(%) | P(%) | S(%) |
|---|---|---|---|---|---|
| Calculated Value (for $C_{18}H_{18}O_3N_3PS$) | 55.81 | 4.68 | 10.85 | 8.00 | 8.28 |
| Found Value | 55.90 | 4.70 | 10.80 | 7.95 | 8.20 |

Tris(4-acetylaminophenyl) thiophosphate was hydrolyzed in the same manner as described above. In this case, however, the addition of methanol was omitted and the reaction time was increased to 6 hours. Consequently, there was obtained 184.0 g of a white crystalline powder melting 153.6°–155° C. This product was tris(4-aminophenyl) thiophosphate having a purity of 98.5% as determined by the diazotization titration method, and its yield was 95%. After completion of the hydrolysis, a sample was taken from the reaction mixture and then analyzed by thin layer chromatography. Thus, the products of partial hydrolysis of tris(4-acetylaminophenyl) thiophosphate still having one or two acetyl groups were found to have disappeared almost completely, but those spots were detected which represented the presence of small amounts of 4-aminophenol and its thiophosphoric mono- and diesters resulting from the hydrolysis of one or more ester linkages of tris(4-aminophenyl) thiophosphate.

EXAMPLE 2

The procedure of Example 1 was repeated except that 248.7 g (0.5 mole) of tris(4-acetylaminophenyl) phosphate was used in place of the tris(4-acetylaminophenyl) thiophosphate. Consequently, there was obtained 176.4 g of a white crystalline powder melting at 153°–155° C. This product was tris(4-aminophenyl) phosphate having a purity of 98.5% as determined by the diazotization titration method, and its yield was 95% based on the amount of tris(4-acetylaminophenyl) phosphate used. The results of elemental analysis of the product were as follows:

|  | C(%) | H(%) | N(%) | P(%) |
|---|---|---|---|---|
| Calculated Value (for $C_{18}H_{18}O_4N_3P$) | 58.22 | 4.89 | 11.32 | 8.34 |
| Found Value | 58.30 | 4.90 | 11.29 | 8.30 |

Tris(4-acetylaminophenyl) phosphate was hydrolyzed in the same manner as described above. In this case, however, the addition of methanol was omitted and the reaction time was increased to 6 hours. Consequently, there was obtained 163 g of a white crystalline powder melting at 152°–155° C. This product was tris(4-aminophenyl) phosphate having a purity of 98.2% as determined by the diazotization titration method, and its yield was 88%. After completion of the hydrolysis, a sample was taken from the reaction mixture and then analyzed by thin layer chromatography. Thus, the products of partial hydrolysis of tris(4-acetylaminophenyl) phosphate still having one or two acetyl groups were found to have disappeared almost completely, but those spots were detected which represented the presence of 4-aminophenol and its phosphoric mono- and diesters resulting from the hydrolysis of one or more ester linkages of tris(4-aminophenyl) phosphate.

EXAMPLE 3

(a) Synthesis of Tris(4-acetylaminophenyl) Thiophosphate

Into a 3-liter four neck flask fitted with a stirrer, a thermometer, a condenser, and a dropping funnel were charged 2,000 ml of acetone (having a water content of 0.2% or less) and 151.2 g (1.0 mole) of 4-acetylaminophenol. Then, 62.7 g (0.37 mole) of phosphorus thiochloride was added to the resulting solution. Immediamount of N-acetylaminophenol used. However, if it is too much, mono- and diesters are formed as by-products. If the amount of phosphorus oxychloride or phosphorus thiochloride used is less than the stoichiometric amount, some of the N-acetylaminophenol reamins unreacted and, therefore, an additional step is required for the recovery thereof. The preferred range of the molar ratio is from 2.5:1 to 3.5:1.

The reaction temperature is preferably 80° C. or below and more preferably from 0° 50° C. If the reaction temperature is higher than this limit, the formation of by-products is undesirably increased as a result of the decomposition of the phosphorus oxychloride or phosphorus thiochloride. If it is too low, the reaction rate is decreased and, therefore, the reaction time is prolonged so as to increase the formation of undesired by-products of hydrolysis. The most preferred range of the reaction temperature is from 20° to 40° C.

The reaction time may vary according to the reaction temperature. Generally, the reaction time is suitably from 1 to 6 hours when the reaction temperature is within the preferred range.

The reaction mixture containing the N-acetylaminoaryl thiophosphate or phosphate so formed may be directly subjected to hydrolysis. Alternatively, prior to hydrolysis, the N-acetylaminoaryl thiophosphate or phosphate may be isolated in the following manner: After completion of the reaction of an N-acetylaminophenol with phosphorus oxychloride or thiochloride, the reaction mixture is vacuum-distilled to remove the solvent therefrom. (Prior to this vacuum distillation, the excess of alkali present in the reaction mixture is preferably neutralized with an acid to prevent the phosphoric or thiophosphoric ester from undergoing hydrolysis.) The resulting concentrate is poured into an alkaline water and the crystals so precipitated are washed with water, so that the hydroxyl-containing by-products such as mono- and diesters are converted into their alkali metal salts which can be dissolved in water and thereby removed. Thus, the desired triester is isolated in a highly pure state.

Procedure B

In this procedure, an anhydrous alkali metal salt of an N-acetylaminophenol is reacted with phosphorus oxychloride or phosphorus thiochloride in an inert organic solvent.

The organic solvent may be any of the organic solvents which have inertness to phosphorus oxychloride or phosphorus thiochloride and can dissolve at least a part of the anhydrous alkali metal salt of N-acetylaminophenol used as a starting material. Specific examples of such organic solvents include ethers such as diethylene glycol dimethyl ether, ethylene glycol dimethyl ether, etc.

The anhydrous alkali metal salt of N-acetylaminophenol can be prepared by reacting an N-acetylaminophenol with sodium or potassium alcoholate. The resulting anhydrous alkali metal salt of N-acetylaminophenol and the phosphorus oxychloride or phosphorus thiochloride are used in a molar ratio ranging from 2.8:1 to 5.0:1. Generally, the anhydrous alkali metal salt of N-acetylaminophenol may as well be used slightly in excess of the stoichiometric amount to prevent the formation of mono- and diesters as by-products. However, if the anhydrous alkali metal salt of N-acetylaminophenol is too much, some of it remains unreacted so as to reduce the efficiency of the reaction. The preferred range of the molar ratio is from 3.0:1 to 3.5:1.

The reaction temperature is suitably from 80° to 140° C. If the reaction temperature is higher than 140° C., large amounts of tarry by-products are undesirably contained in the reaction product. If it is lower than 80° C., the reaction rate is too low for practical purpose. The preferred range of the reaction temperature is from 100° to 120° C.

The reaction time may vary according to the reaction temperature. Generally, the reaction is from 8 to 16 hours when the reaction temperature is within the preferred range.

The reaction mixture containing the N-acetylaminoaryl thiophosphate or phosphate so formed may be directly subjected to hydrolysis. Alternatively, prior to hydrolysis, the N-acetylaminoaryl thiphosphate or phosphate may be isolated in the following manner: After completion of the reaction of an anhydrous alkali metal salt of an N-acetylaminophenol with phosphorus oxychloride or phosphorus thiochloride, the reaction mixture is filtered, while hot, to remove the resulting insoluble salt and unreacted alkali metal salt of N-acetylaminophenol. Then, the filtrate is vacuum-distilled to remove the solvent therefrom. The resulting concentrate is poured into an alkaline water and the crystals so precipitated are washed with water, so that the hydroxyl-containing by-products such as mono- and diesters are converted into their alkali metal salts which can be dissolved in water and thereby removed. Thus, the desired triester is isolated in a highly pure state.

The aminoaryl thiophosphates or phosphates prepared by the process of the invention, which have one or more primary amino groups, can be reacted with phosgene to produce the corresponding isocyanates that are useful as coating materials, adhesives, and the like. This is suitably accomplished by the commonly used two-stage phosgenation method which is carried out under cold and hot conditions. Alternatively, the method involving the phosgenation of an amine hydrochloride may be carried out in the following manner: After completion of the above-described hydrolysis, the reaction mixture (consisting of an aqueous solution of a primary amine hydrochloride) is cooled to a temperature of from 5° to 10° C. without being neutralized. The primary amine hydrochloride so precipitated is separated, for example, by filtration and then dissolved in a suitable solvent. After the water is removed by azeotropic distillation, the resulting solution is subjected to a common phosgenation procedure.

The present invention will be more fully understood by reference to the following examples. However, these examples are intended merely to illustrate the practice of the invention and are not to be construed to limit the scope of the invention.

EXAMPLE 1

(a) Synthesis of Tris (4-acetylaminophenyl) Thiophosphate

Into a 3-liter flask fitted with a stirrer, a thermometer, a dropping funnel, and a condenser were charged 136.2 g (0.9 mole) of 4-acetylaminophenol and 2,160 g of acetone. The contents were stirred at room temperature for 30 minutes to form a solution. While this solution was being externally cooled to 10°–15° C. and stirred at a high speed (700 r.p.m.), 77.1 g (0.93 mole) of a 48.2% aqueous solution of sodium hydroxide was added ately after that, 96 g (1.08 moles) of a 45% aqueous solution of sodium hydroxide was added thereto dropwise, with vigorous stirring, through the dropping funnel. This addition was carried out over a period of about 5 minutes, during which external cooling was used to keep the reaction temperature at 30° C. Then, the reaction was carried out at that temperature for 5 hours. After the acetone was distilled off at 30° C. under reduced pressure, the resulting concentrate was poured into 2,000 g of a ca. 5% aqueous solution of sodium hydroxide cooled to 10° C. or below. The precipitate so formed was separated by filtration, washed with water, and then vacuum-dried at 60°–80° C. for 12 hours to obtain 157.3 g of a white crystalline product melting at 194°–196° C. This product was tris(4-acetylaminophenyl) thiophosphate and its yield was 92% based on the amount of 4-acetylaminophenol used. It was further purified by recrystallization from methanol and then subjected to elemental analysis. The results thus obtained were as follows:

|  | C(%) | H(%) | P(%) | S(%) | N(%) |
|---|---|---|---|---|---|
| Calculated Value (for $C_{24}H_{24}O_6N_3PS$) | 56.14 | 4.70 | 6.03 | 6.24 | 8.18 |
| Found Value | 56.23 | 4.65 | 6.00 | 6.21 | 8.21 |

(b) Hydrolysis of Tris(4-acetylaminophenyl) Thiophosphate

Into a 1-liter four neck flask fitted with a stirrer, a thermometer, and a dropping funnel were charged 150.0 g of tris(4-acetylaminophenyl) thiophosphate, 320 g of 35% hydrochloric acid, 180 g of water, and 30 g of methanol. The resulting reaction mixture was heated to 85° C. and the hydrolysis was carried out at that temperature, during which the reaction mixture remained in the form of a slurry. After the hydrolysis was continued for 3 hours, a sample was taken from the reaction mixture, neutralized with sodium hydroxide, and then analyzed by thin layer chromatography. Thus, insufficiently hydrolyzed intermediate products (or the products of partial hydrolysis of tris(4-acetylaminophenyl) thiophosphate still having one or two acetyl groups) were found to have disappeared almost completely and a spot representing the presence of a very small amount of 4-aminophenol was observed. The hydrolysis was stopped at that time, and the reaction mixture was cooled to room temperature and then neutralized to pH 7.2 with a 45% aqueous solution of sodium hydroxide. The precipitate so formed was separated by filtration, washed with water, and then dried to obtain 111.0 g of a white crystalline powder melting at 154.6°–156.2° C. This product was tris(4-aminophenyl) thiophosphate having a purity of 98.9% as determined by the diazotization titration method, and its yield was 98.0% based on the amount of tris(4-acetylaminophenyl) thiophosphate used or 90.2% based on the amount of 4-acetylaminophenol used. The results of elemental analysis of the product were as follows:

|  | C(%) | H(%) | N(%) | P(%) | S(%) |
|---|---|---|---|---|---|
| Calculated Value (for $C_{18}H_{18}O_3N_3PS$) | 55.81 | 4.68 | 10.85 | 8.00 | 8.28 |
| Found Value | 55.76 | 4.66 | 10.73 | 7.92 | 8.13 |

Tris(4-acetylaminophenyl) thiophosphate was hydrolyzed in the same manner as described above. In this case, however, the addition of methanol was omitted. Six hours were required for insufficiently hydrolyzed intermediate products to disappear. Consequently, there was obtained 107.6 g of a white crystalline powder melting at 152.6°–155.0° C. This product was tris(4-aminophenyl) thiophosphate having a purity of 98.2% as determined by the diazotization titration method, and its yield was 95%

EXAMPLE 4

Tris(4-acetylaminophenyl) thiophosphate was synthesized in the same manner as described in Example 3. After the acetone was distilled off at about 60° C. under normal pressure, hydrochloric acid, water, and methanol were added to the resulting concentrate in the same proportions as used in Example 3, and the hydrolysis was carried out. The reaction mixture was cooled to 10° C. and then adjusted to pH 11 by dropwise addition of a 45% aqueous solution of sodium hydroxide. The precipitate so formed was separated by filtration, washed with water, and then dried to obtain 117 g of a yellowish-white crystalline powder melting at 153.5°–156.1° C. This product was tris(4-aminophenyl) thiophosphate having a purity of 98.3% as determined by the diazotization titration method, and its yield was 90.6% based on the amount of 4-acetylaminophenol used. When the alkaline filtrate was analyzed by thin layer chromatography, it was found to contain the thiophosphoric mono- and diesters of 4-aminophenol resulting from the aforesaid condensation reaction and hydrolysis.

EXAMPLE 5

The procedure of Example 4 was repeated except that 55.2 g (0.36 mole) of phosphorus oxychloride was used in place of the phosphorus thiochloride. Consequently, there was obtained 96.5 g of a yellowish-white crystalline product melting at 152.8°–155.1° C. This product was tris(4-aminophenyl) phosphate having a purity of 98.0% as determined by the diazotization titration method, and its yield was 78% based on the amount of 4-acetylaminophenol used. It was further purified by recrystallization from methanol and then subjected to elemental analysis. The results thus obtained were as follows:

|  | C(%) | H(%) | N(%) | P(%) |
|---|---|---|---|---|
| Calculated Value (for $C_{18}H_{18}O_4NP$) | 58.22 | 4.89 | 11.32 | 8.34 |
| Found Value | 58.15 | 4.91 | 11.27 | 8.22 |

EXAMPLE 6

(a) Synthesis of Tris(4-acetylaminophenyl) Thiophosphate

Into a 3-liter four neck flask fitted with a stirrer, a thermometer, and a condenser was charged 1,000 ml of methanol, and 23.0 g (1.0 mole) of metallic sodium was added thereto and dissolved therein by stirring at 65° C. Then, 151.2 g (1.0 mole) of 4-acetylaminophenol was added thereto and dissolved therein by stirring at 50° C. for 30 minutes. From the resulting solution of 4-acetylaminophenol sodium, the methanol was removed by distillation. Then, 2,000 ml of diethylene glycol dimethyl ether was added thereto to form a slurry, which was heated to 120° C. Thereafter, 55.9 g (0.33 mole) of phosphorus thiochloride was added thereto over a period of 10 minutes, and the reaction was carried out at 120° C. for 12 hours. While hot, the reaction mixture was filtered to remove unreacted 4-acetylaminophenol sodium and sodium chloride formed as a by-product of the esterification reaction. After the solvent was distilled off under reduced pressure, the resulting concentrate was poured into 3,000 g of a ca. 5% aqueous alkaline solution cooled to 10° C. The precipitate so formed was separated by filtration, washed with water, and then vacuum-dried at 60°-80° C. for 12 hours to obtain 144.0 g of a yellowish-white crystalline product melting at 192°-194° C. This product was tris(4-acetylaminophenyl) thiophosphate and its yield was 85% based on the amount of phosphorus thichloride used. It was further purified by recrystallization from methanol and then subjected to elemental analysis. The results thus obtained were as follows:

|  | C(%) | H(%) | P(%) | S(%) | N(%) |
|---|---|---|---|---|---|
| Calculated Value (for $C_{24}H_{24}O_6N_3PS$) | 56.14 | 4.70 | 6.03 | 6.24 | 8.18 |
| Found Value | 56.20 | 4.68 | 6.00 | 6.20 | 8.11 |

(b) Hydrolysis of Tris(4-acetylaminophenyl) Thiophosphate

Into a 1-liter four neck flask fitted with a stirrer, a thermometer, and a dropping funnel were charged 150 g of tris(4-acetylaminophenyl) thiophosphate, 320 g of 35% hydrochloric acid, 180 g of water, and 30 g of methanol. The resulting reaction mixture was heated to 85° C. and the hydrolysis was carried out at that temperature, during which the reaction mixture remained in the form of a slurry. After the hydrolysis was continued for 3 hours, a sample was taken from the reaction mixture, neutralized with sodium hydroxide, and then analyzed by thin layer chromatography. Thus, insufficiently hydrolyzed intermediate products (or the products of partial hydrolysis of tris(4-acetylaminophenyl) thiophosphate still having one or two acetyl groups) were found to have disappeared almost completely and a spot representing the presence of a very small amount of 4-aminophenol was observed. The hydrolysis was stopped at this time, and the reaction mixture was cooled to room temperature and then neutralized to pH 7.2 with a 45% aqueous solution of sodium hydroxide. The precipitate so formed was separated by filtration, washed with water, and then dried to obtain 111.0 g of a white crystallie powder melting at 154.1°-156.5° C. This product was tris(4-aminophenyl) thiophosphate having a purity of 98.3% as determined by the diazotization titration method, and its yield was 98.0% based on the amount of tris(4-acetylaminophenyl) thiophosphate used or 83.3% based on the amount of phosphorus thiochloride used. The results of elemental analysis of the product were as follows:

|  | C(%) | H(%) | N(%) | P(%) | S(%) |
|---|---|---|---|---|---|
| Calculated Value (for $C_{18}H_{18}O_3N_3PS$) | 55.81 | 4.68 | 10.85 | 8.00 | 8.28 |
| Found Value | 55.80 | 4.65 | 10.80 | 7.95 | 8.20 |

EXAMPLE 7

The procedure of Example 6 was repeated except that 50.6 g (0.33 mole) of phosphorus oxychloride was used in place of the phosphorus thiochloride. Consequently, there was obtained 85.8 g of a yellowish-white crystalline product melting at 153°-155° C. This product was tris(4-aminophenyl) phosphate having a purity of 98% as determined by the diazotization titration method, and its yield was 70% based on the amount of phosphorus oxychloride used. It was further purified by recrystallization from methanol and then subjected to elemental analysis. The results thus obtained were as follows:

|  | C(%) | H(%) | N(%) | P(%) |
|---|---|---|---|---|
| Calculated Value (for $C_{18}H_{18}O_4NP$) | 58.22 | 4.89 | 11.32 | 8.34 |
| Found Value | 58.00 | 4.95 | 11.20 | 8.15 |

What is claimed is:

1. A process for the preparation of an ester compound selected from the group consisting of tris(aminoaryl)thiophosphates and tris(aminoaryl)phosphates which comprises the steps of
    (a) reacting an N-acetylaminophenol with phosphorus oxychloride or phosphorus thiochloride in a molar ratio of 2.5 to 3.5:1, in the presence of an alkali metal hydroxide or carbonate, water and an inert organic solvent selected from the group consisting of aliphatic ketones and ethers, at a temperature of 80° C. or below to form tris-(acetylaminoaryl)thiophosphate or tris-(acetylaminoaryl)phosphate; and
    (b) hydrolyzing said tris(N-acetylaminoaryl)thiophosphate or tris(N-acetylaminoaryl)phosphate by heating it without separation treatment at a temperature of from 50° to 100° C. in an aqueous solution of a mineral acid having a concentration of from 5 to 30% by weight to form said ester compound.

2. A process for the preparation of an ester compound selected from the group consisting of tris(aminoaryl)thiophosphates and tris(aminoaryl)phosphates which comprises hydrolyzing a starting material by heating it at a temperature of from 50° to 100° C. in an aqueous solution of a mineral acid having a concentration of from 5 to 30% by weight to form the ester compound, the starting material being selected from the group consisting of tris(N-acetylaminoaryl)thiophosphates and tris(N-acetylaminoaryl)phosphates.

3. The process according to claim 2 wherein the heating of the starting material in an aqueous solution of a mineral acid is carried out in the copresence of an alcohol.

4. The process according to claim 3 wherein the alcohol is a lower aliphatic monohydric alcohol.

5. The process according to claim 4 wherein the alcohol is methanol, ethanol, or isopropanol.

6. The process according to claim 2 wherein the amount of alcohol used is at least one equivalent per mole of the acetyl group contained in the starting material.

7. The process according to claim 6 wherein the amount of alcohol used is from 0.5 to 2 equivalents per mole of the acetyl group.

8. The process according to claim 2 wherein the mineral acid is hydrochloric acid and the aqueous solution thereof has a concentration of from 15 to 25% by weight.

9. The process according to claim 8 wherein the amount of hydrochloric acid used is at least one equivalent per mole of the acetyl group contained in the starting material.

10. The process according to claim 9 wherein the amount of hydrochloric acid used is from 3 to 5 equivalents per mole of the acetyl group.

11. The process according to claim 2 wherein the hydrolysis is carried out at a temperature of from 70° to 90° C.

12. The process according to claim 2 wherein the starting material is tris(4-acetylaminophenyl) thiophosphate or tris(4-acetylaminophenyl) phosphate and the ester compound is tris(4-aminophenyl) thiophosphate or tris(4-aminophenyl) phosphate.

13. The process according to claim 2 wherein the amount of the mineral acid used is at least one equivalent per mole of the acetyl group contained in the starting material.

14. The process according to claim 13 wherein the amount of the mineral acid used is from 3 to 10 equivalents per mole of the acetyl group contained in the starting material.

15. A process for the preparation of an ester compound selected from the group consisting of tris(aminoaryl)thiophosphates and tris(aminoaryl)phosphates which comprises hydrolyzing a starting material selected from the group consisting of tris(N-acetylaminoaryl)thiophosphates and tris(N-acetylaminoaryl)phosphates by heating it at a temperature of from 50° to 100° C. in an aqueous solution of mineral acid having a concentration of from 5 to 30% by weight in the copresence of an alcohol to form said ester compound, the amounts of said mineral acid and said alcohol being at least one equivalent per mole of the acetyl group contained in said starting material, respectively.

* * * * *